(12) United States Patent
Lee et al.

(10) Patent No.: US 6,676,973 B1
(45) Date of Patent: Jan. 13, 2004

(54) METHOD OF TREATING OVARIAN CANCERS WITH CADMIUM

(75) Inventors: Kang Bo Lee, North Potomac, MD (US); Ricardo J. Parker, Washington, DC (US); Eddie Reed, Germantown, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 08/398,460

(22) Filed: Mar. 3, 1995

(51) Int. Cl.[7] .................. A61K 33/24; A61K 31/28
(52) U.S. Cl. .................. 424/649; 424/654; 514/505
(58) Field of Search .................. 424/649, 654; 514/505, 649

(56) References Cited

U.S. PATENT DOCUMENTS 5,635,479 A * 6/1997 Jacob et al. .................. 514/12

OTHER PUBLICATIONS

Carter et al, Chemotherapy of Cancer 2nd Ed, p 362–365 (1981).*
Carter et al., Chemotherapy of Cancer, 2nd Ed. John Wiley & Sons, N.Y., N.Y., 1981, pp. 107–108.*
M. P. Waalkes et al., *Toxicology and Applied Pharmacology,* 110, pp. 327–335 (1991).
Proceedings of the 85th Annual Meeting of the American Association for Cancer Research, vol. 35, Mar. 1994.
T. Ochi et al., *Mutation Research,* 180, pp 257–266 (1987).
M. P. Waalkes et al., *Metallothionein,* "Tumor Suppressive Activity of Cadmium," Birkhauser Verlag, Basel, Switzerland (1993). pp. 1–12.
M. P. Waalkes et al., *Critical Reviews in Toxicology,* 22 (3,4), pp. 175–201 (1992).

* cited by examiner

Primary Examiner—Jerome D. Goldberg
(74) Attorney, Agent, or Firm—Birch, Stewart, Kolasch & Birch, LLP (57) ABSTRACT

A method is provided for treating an ovarian cancer in a human or other mammalian patient suffering from the ovarian cancer, the method comprises administering to the human or the other mammalian patient an effective ovarian cancer treating amount of cadmium, preferably in the form of cadmium chloride.

Pharmaceutical compositions and pharmaceutical kits which are useful in practicing the described method of treating ovarian cancer in the human or other mammalian patient suffering from the ovarian cancer are also provided for in the disclosure.

7 Claims, 5 Drawing Sheets

Time During One Hour Drug Exposure (Minutes)

FIGURE 3B

Time After One Hour Drug Exposure (Hours)

METHOD OF TREATING OVARIAN CANCERS WITH CADMIUM

FIELD OF THE INVENTION

The present invention is concerned with providing an advantageous method of treating an ovarian cancer by administering a pharmaceutically acceptable cadmium containing compound to a human or other mammalian patient suffering from an ovarian cancer.

Pharmaceutical compositions and Pharmaceutical kits which are useful in practicing the method of ovarian cancer treatment are also provided.

BACKGROUND OF THE INVENTION

Cadmium is a highly toxic non-essential transition metal that constitutes an important potential health risk to the environment. Cadmium has been characterized as a potent carcinogen in animals, and is presumed to be carcinogenic in humans, as evidenced in epidemiological studies of workers occupationally exposed to this heavy metal [1]. Studies of the metabolism of Cadmium in rodent tissues and organs suggest that the mechanism of its toxic effect may be through induction of abnormal protein synthesis [3]. The modulation of Cadmium toxicity may be mediated through metallothionein and glutathione [4–7]. In cell culture, Cadmium has been shown to be cytotoxic [6, 8–10], mutagenic [10–13], and capable of inducing cellular transformation [3]. Cadmium interacts with cellular macromolecules and modifies the metabolism of DNA, RNA and protein [14], any of which could account for the cytotoxic effect of Cadmium at the molecular level. Surprisingly, several animal studies have shown that Cadmium is associated with suppression of tumor development. Waalkes and colleagues, examining the tumor promoting effect of Cd in B6C3F1 mice treated with the lung and liver tumor promotor N-nitrosodiethylamine (NDEA), unexpectedly found that Cadmium prevented NDEA-induced tumor formation [4,16]. In that study, it was shown that a single dose of NDEA followed by cadmium chloride in the drinking water, eliminated spontaneously-occurring liver tumors and reduced the incidence and multiplicity of NDEA-induced lung tumors in these mice. This Cadmium-induced tumor suppression effect on B6C3F1 mouse liver and lung occurred regardless of the time period of Cadmium administration.

These investigators suggested that the tumor suppressive effect of Cadmium may possibly be due to a specific toxicity toward previously "initiated" tumor cells within the mouse liver and lung. Histologic examination of NDEA-induced hepatic and pulmonary lesions in these mice revealed a marked and specific deficiency of metallothionein levels in tumor cells. In addition, the hepatic lesions responded abnormally to the induction of metallothionein compared to normal tissue surrounding the lesions. This suggests that transformation-initiated cells acquired this tumor suppression effect by Cadmium. The molecular mechanisms involved in the Cadmium-induced tumor suppression is unknown.

SUMMARY OF THE INVENTION

The present invention is concerned with providing an advantageous method for treating ovarian cancer in a human or other mammalian patient suffering from ovarian cancer, by administering to said patient an effective ovarian cancer treating amount of a pharmaceutically acceptable cadmium containing compound, optionally in combination with an effective ovarian cancer treating amount of cisplatin.

The present invention is also concerned with providing a pharmaceutical composition which comprises an effective ovarian cancer treating amount of a pharmaceutically acceptable cadmium containing compound, and a pharmaceutically acceptable carrier therefor, which may be used in practicing the advantageous method for treating ovarian cancer which is disclosed herein.

The present invention is also concerned with providing a kit which is useful in the treatment of ovarian cancer in a human or other mammalian patient suffering from ovarian cancer, wherein the kit comprises: (a) a pharmaceutical composition which comprises an effective ovarian cancer treating amount of a pharmaceutically acceptable cadmium containing compound, and a pharmaceutically acceptable carrier therefor, (b) optionally a pharmaceutical composition which comprises an effective ovarian cancer treating amount of cisplatin, and a pharmaceutically acceptable carrier therefor, and (c) instructions for providing an advantageous method for treating ovarian cancer in a human or other mammalian patient suffering from ovarian cancer, by administering to said patient the pharmaceutical composition comprising the effective ovarian cancer treating amount of the pharmaceutically acceptable cadmium containing compound, and optionally by administering in combination therewith to the patient the pharmaceutical composition comprising the effective ovarian cancer treating amount of cisplatin.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 3A represents the cellular accumulation of Cd. FIG. 3B represents the percentage of Cd drug efflux.

DETAILED DESCRIPTION OF THE INVENTION

The following detailed description is provided as an aid to those desiring to practice the present invention. It is not to be construed as limiting to the present inventive discovery, since those of ordinary skill in the art will realize that modifications can be made in the materials and procedures set forth herein without departing from the spirit or scope of the present inventive discovery. Accordingly, the present invention is only to be limited by the scope of the claims appended hereto and the equivalents thereof.

In order to further aid those desiring to practice the present invention, the following is a glossary of abbreviations that are used herein.

AAS: atomic absorption spectrometry
$IC_{50}$: dose of drug that reduces survival in a cell line to 50% of the control group
Cd-DNA: cadmium-DNA adduct
GSH: glutathione
Cd: cadmium The following portion of this detailed description of the present invention is divided into the following sub-headings for the reader's convenience and in an effort to better set forth the different inventive embodiments of the present inventive discovery, which are encompassed hereby.

I. Method of Treating Ovarian Cancer
II. Pharmacological Test Examples
   (Including Tables of Test Results and Related Discussions)
III. Pharmaceutical Compositions
IV. Pharmaceutical Kits
V. References
   (List of Publications and Other Documents Cited in the Present Disclosure).

I. Method of Treating Ovarian Cancer

As indicated above the present invention is concerned with providing an advantageous method for treating ovarian cancer in a human or other mammalian patient that is suffering from ovarian cancer. The method generally entails administering a pharmaceutically acceptable cadmium containing compound to the patient in an amount effective for treating the ovarian cancer in the patient suffering therefrom. Usually the cadmium containing compound is administered to the patient in the form of a pharmaceutical composition, as described herein, but the same is not mandatory, since it is entirely possible that a pharmaceutically acceptable cadmium containing compound per se may be administered to a patient suffering from ovarian cancer and effectively treat the patient's ovarian cancer.

In order to effectively treat ovarian cancer in a patient suffering therefrom, the present invention also encompasses administering an effective ovarian cancer treating amount of a cadmium containing compound to the patient in combination with other compounds which are know to be effective in treating ovarian cancer. Exemplary of such compounds is cisplatin. In this respect it is envisioned that the co- or joint-administration of a cadmium containing compound and cisplatin to a patient suffering from ovarian cancer, in a total amount as provided for hereinbelow, may help to alleviate side-effects that might otherwise be associated with either the sole administration of either the cadmium containing compound or cisplatin to the patient, since cadmium and cisplatin are both know to have toxic properties, even if they are both effective in treating ovarian cancer in a human or other mammalian patient suffering therefrom.

In practicing the inventive methods of treating ovarian cancer disclosed herein, the exact individual dosages, as well as the daily dosages of the cadmium containing compound to be administered to the patient suffering from ovarian cancer are generally to be determined on a case by case basis in accordance with standard medical principles under the direction of a physician or veterinarian, as described hereinbelow. However, in order to aid those desiring to practice the present inventive methods, there is also provided hereinbelow information on suitable pharmaceutical compositions, and dosages of cadmium containing compounds which may be advantageously used in the present inventive methods.

The efficacy of the methods of the present invention in treating ovarian cancer in a patient suffering therefrom, and the ability of a physician or veterinarian skilled in the art to effectively treat ovarian cancer in a human or other mammalian patient, respectively, using a pharmaceutically acceptable cadmium containing compound, will become more apparent upon review of the following pharmacological test examples, and the discussions which are provided related thereto.

II. Pharmacological Test Examples
(Including Tables of Test Results and Related Discussions)

Cd is regarded as one of the most toxic trace elements in the environment. Numerous reports implicate Cd as a potent carcinogen and mutagen in mammals [11, 13, 23]. However, recently and quite surprisingly, Cd has been shown to have tumor suppressive effects as well.

Cd is known to interact with a variety of sites in the cell where essential metals such as Zn, Cu, and Ca play a role in normal metabolic functions. The replacement of these essential metals with Cd can cause a wide variety of Cd-induced biological alterations in both structure and function of cellular macromolecules, leading to cytotoxicity or carcinogenesis [24–27]. The mechanisms underlying cytotoxic effects of Cd is poorly understood. Several studies by Ochi and colleagues suggest the involvement of a Cd-induced active oxygen species [14, 28–30]. Exposure of cultured Chinese hamster V79 cells to CdCl induced a prooxidant state (i.e., produced active oxygen) in these cells, and inhibited cell growth and DNA synthesis, as well as induced clastogenesis. In these cells, Cd did not influence the enzymes that constitute the scavengers of active oxygen (i.e., superoxide dismutase, catalase, GSH-peroxidase, and GSSG-reductase) [29]. However, the inhibitory effects of Cd were suppressed in part by catalase, butylated hydroxytoluene (a diffusible radical scavenger) and D-mannitol (a hydroxyl radical scavenger). D-mannitol exerted significant suppression of Cd-induced inhibition of cell growth and DNA synthesis [29]. In addition, in cells exposed to 20 $\mu$M Cd, the levels of GSH were decreased, while cellular RNA and protein synthesis was not so influenced [28, 29]. This Cd-induced GSH decrease is suggested to be responsible for the role active oxygen plays in the observed Cd-induced alterations. These studies suggest the presence of a unique mechanism underlying the action of Cd, whereby active oxygen and free radicals may play a potential role as mediators in the induction of cytotoxicity, mutagenicity and carcinogenicity.

Figure 5A:
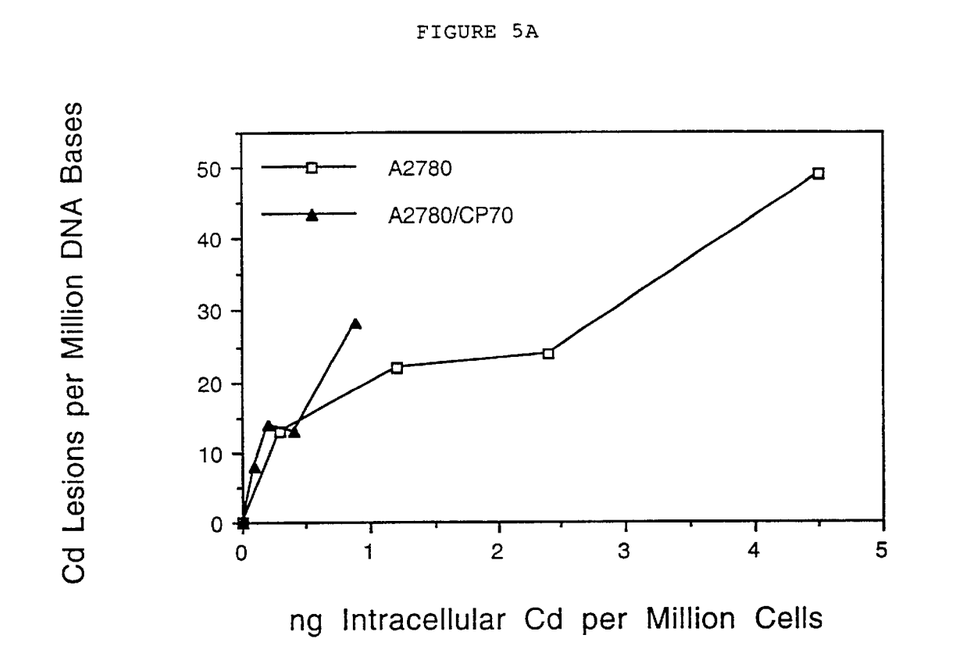
FIGS. 5A and 5B—Relationship between DNA damage and intracellular drug (FIG. 5A) and between cytotoxicity and DNA-damage (FIG. 5B) in human ovarian cancer A2780/CP70 cells.
Figure 5B:
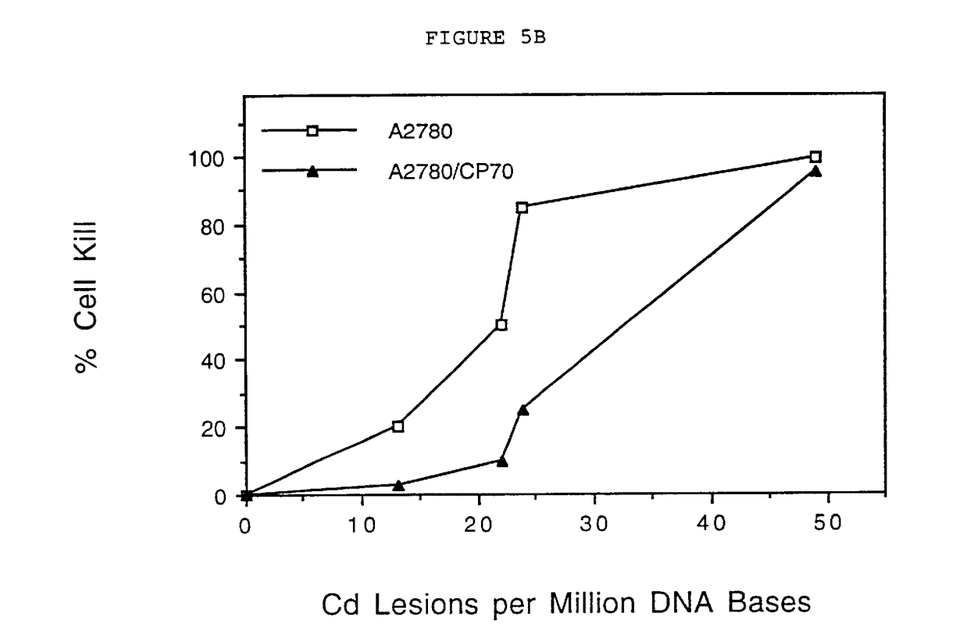

In another study, Ochi and co-workers [14] demonstrated in cultured Chinese hamster ovary cells the ability of CdCl to induce single strand breaks in cellular DNA. This also involved the action of the Cd-generated active oxygen species, which induced DNA damage, DNA-protein crosslinks, and DNA-repair inhibition. Cd may also interact directly with DNA and/or indirectly by interfering with genetic controls or repair mechanisms as a result of Cd-protein interactions [11]. We present herein, the first demonstration of a direct association between Cd-DNA damage, and cellular cytotoxicity (FIG. 5).

Toxic metals in general compete with essential metals at chelation sites and interfere with normal functioning of those chelate molecules by forming irreversible and stable bonds—a primary alteration leading to various biological consequences. To date, the mechanism(s) of Cd's action as well as its cytotoxic (or carcinogenic) target(s) is unclear. However, in rodent studies, following Cd exposure, the metal was observed to be initially concentrated in nuclei of various organs, with a substantial portion bound to DNA[31, 32]. The direct interactions of metals like Cd, Mg, Zn and Ca with DNA is thought to involve two distinct sites in the DNA molecule, in which contain two basic classes of metal-binding sites. Metals appear to interact with both phosphate groups and various electron donor groups of bases in DNA [33–35]. Waalkes and Poirier investigated the binding kinetics/interactions of Cd and essential metals Mg, Ca and Zn with isolated calf thymus DNA, and characterized two Cd-binding sites on double stranded DNA. These sites were heat unstable high affinity (HA) binding sites that showed 0.093 $\mu$mol of HA sites/mg DNA (0.031 sites per DNA base) [26]. These HA sites exhibited positive cooperative binding at bound-Cd concentration $\geq 1.4$ $\mu$M. Ca, Mg, and Zn were shown to be competitive antagonist of Cd binding to HA sites (Zn>Mg>Ca). Interestingly, the relative capability of these essential metals to antagonize Cd-DNA binding in vitro corresponds with their ability to prevent Cd-induced tumor formation in vivo [2, 15 and 36].

The primary cellular target for Cd appears to be cellular DNA, whereby the inhibition of DNA synthesis has been cited as the probable cytotoxic event. Studies by Nocentini, with human and simian cells treated with Cd following UV-irradiation, demonstrated that the level and mechanism of action of Cd on cellular metabolism may be through the preferential inhibition of DNA synthesis [12]. In a series of experiments, it was shown that Cd reversibly inhibited DNA replication and repair capability in these cells. Cd also inhibited the rates of recovery of RNA and protein syntheses in cells impaired by UV-irradiation. This inhibitory effect was suggested to occur through the competitive displacement of zinc by Cd at common binding sites on zinc-requiring enzymatic proteins involved in DNA and RNA synthesis. However, data presented in the current work, suggests that perturbation of DNA and RNA function may also result from direct Cd-induced DNA damage.

Acquired cisplatin resistance in human ovarian cancer cells was derived from continuous stepwise exposure of human ovarian cancer A2780 cells to cisplatin, and the characteristic phenotype associated with these cells has been described [17, 18]. The biological profile of Cd in these cell lines appears to somewhat resemble cisplatin, in that resistant cells exhibit reduced cellular Cd accumulation, that is associated with reduced Cd-DNA damage. In the case of cisplatin, however, enhanced DNA repair in resistant cells is a major contributor to the differential in cellular resistance [18]. Also, elevated cellular levels of glutathione (GSH) and/or metallothionein may contribute to cellular resistance to cisplatin [5, 15], resulting in cytosolic inactivation of drug. This is probably also true for Cd in these cells. Such similarities and differences, suggest the possibility of the use of Cd as a potential anti-cancer chemotherapeutic agent.

In order to show the efficacy of the present inventive methods, we examined Cadmium's effect on cisplatin resistant human ovarian cancer A2780/CP70 cells and its cisplatins sensitive parental cell line A2780. The A2780/CP70 cell line is a resistant subline developed by chronic stepwise exposure of A2780 cells to cisplatin [17, 18]. A2780/CP70 cells exhibit an acquired cisplatin resistance profile that is associated with reduced cellular drug accumulation, reduced DNA platination, and enhanced repair of cisplatin-induced DNA lesions compared to cisplatin sensitive A2780 cells [18]. We examined the effects of Cd on cellular sensitivity, cellular drug accumulation and efflux, and Cd-DNA adduct formation and repair.

1. MATERIALS AND TEST METHODS

1.1. Cell Growth and Cytotoxicity Studies

Human ovarian cancer A2780 and A2780/CP70 cells were cultured in monolayer using RPMI 1640 media supplemented with 10% fetal calf serum, 2 mM L-glutamine, 0.2 U insulin/ml, 100 U/ml penicillin, and 100 $\mu$g/ml streptomycin (GIBCO, Grands Island, N.Y.). Cells were grown in a humidified chamber containing a mixture of 5% $CO_2$ and ambient air at 37° C. Sensitivity of A2780 and A2780/CP70 cells to Cd and to cisplatin was assessed by microculture tetrazolium (MTT) assay, as described by Alley et al [19]. Briefly, cells were plated at 1000 cells/well in 96-well plates and drug exposure was made the following day. Cadmium dichloride was initially dissolved in double distilled water ($Dh_2O$) at 1.0 mg/ml (5.46 Mm Cadmium), and dilutions from this solution were made in media to obtain the desired drug treatment concentrations of 1 $\mu$M, 10 $\mu$M, 20 $\mu$M, 40 $\mu$M, 100 $\mu$M, 150 $\mu$M and 200 $\mu$M. Cisplatin was dissolved in PBS without $Ca^{++}$ or $Mg^{++}$ at 1.0 mg/ml (3.33 Mm cisplatin), and dilutions from this solution was made in media to obtain the desired drug treatment concentrations of ranging from 1 $\mu$M to 300 $\mu$M. Drug treatments were for 1 hour.

After drug treatments, cells were washed twice with PBS without $Ca^{++}$ or $Mg^{++}$, treated with fresh drug-free media, and incubated for 5 days. On day 5 after drug treatment, 50 microliter of 3-(4,5-dimethylthiazol-2-yl)-2,5 diphenyltetrazolium bromide (MTT) (400 mg in 200 ml of PBS) were added to each well and incubated for 4 hours at 37° C. Analysis of optical density readings were performed using the VV Deltasoft program on a Macintosh computer (Apple, Inc., Palo Alto, Calif.) and percentage cell growth values were obtained.

1.2. Measurement of Cellular Cadmium Accumulation

We examined the cellular Cd accumulation following 1 hour exposures to a range of Cd doses. Cells were grown in T-150 flasks (Costar, Cambridge, Mass.) to 60–80% confluence and then exposed to 10 $\mu$M, 50 $\mu$M, 100 $\mu$M and 200 $\mu$M Cd for 1 hour. Cells were harvested, immediately counted and then "wet-ashed" [20]. Total cellular Cd accumulation was measured by atomic absorption spectrometry with Zeeman background correction (AAS) [21], and assessed as nanograms of Cd per million cells (ng Cd/$10^6$ cells)

1.3 Measurement of Cellular Drug Accumulation and Efflux

A2780 and A2780/CP70 cell lines were treated at their $IC_{50}$ drug doses of 58 $\mu$M and 128 $\mu$M Cd, respectively, for the purpose of measuring cellular Cd accumulation and efflux. Cells were harvested at time points of 15, 30, 45, and 60 minutes during 1 hour drug exposures, and at 1 and 3 hours after drug exposure. Cells were immediately counted and then wet-ashed. Total cellular drug. accumulation was measured by AAS, and assessed as both nanograms of Cd per million cells (ng Cd/$10^6$ cells) and as the percentage of the highest levels of total cellular drug.

1.4. Measurement of Cadmium in Cellular DNA

We examined the formation of Cd-DNA adduct in cellular DNA following 1 hour exposures to a range of Cd drug doses. Cells were grown in T-150 flasks (Costar, Cambridge, Mass.) to 60–80% confluence and then exposed to 0 μM (control), 10 μM, 50 μM, 100 μM and 200 μM Cd for 1 hour. Following a 1 hour drug exposure, cells were washed twice with cold PBS, harvested, and frozen immediately at −20° C. until DNA isolation. Total cellular DNA was isolated on cesium chloride density gradients [22]. DNA was dialyzed against $Dh_2O$ with 3–4 changes over 36–48 hours, and quantitated by absorbance at 260 nm. Total Cd per unit DNA was measured by AAS.

1.5 Cadmium-DNA Adduct Formation and Repair

We examined the formation and removal of Cd-DNA adduct in cellular DNA following 1 hour drug exposures. A2780 and A2780/CP70 cells were grown in T-150 flasks (Costar, Cambridge, Mass.) to 60–80% confluence, and then exposed to their $IC_{50}$ doses of 58 μM and 128 μM, respectively. An aliquot of cells was harvested before drug treatment (time zero). Following a 1 hour drug exposure, cells were washed and harvested at. the following time points: 0 hour (immediately at the end of Cd exposure), 1 hour, 6 hour, and 24 hours. Cells were frozen immediately at −20° C. until DNA isolation. Total cellular DNA was isolated and assayed as described above, and total Cd per unit DNA was measured by AAS.

2. RESULTS

2.1 Cellular Sensitivity to Cadmium

Figure 1A:
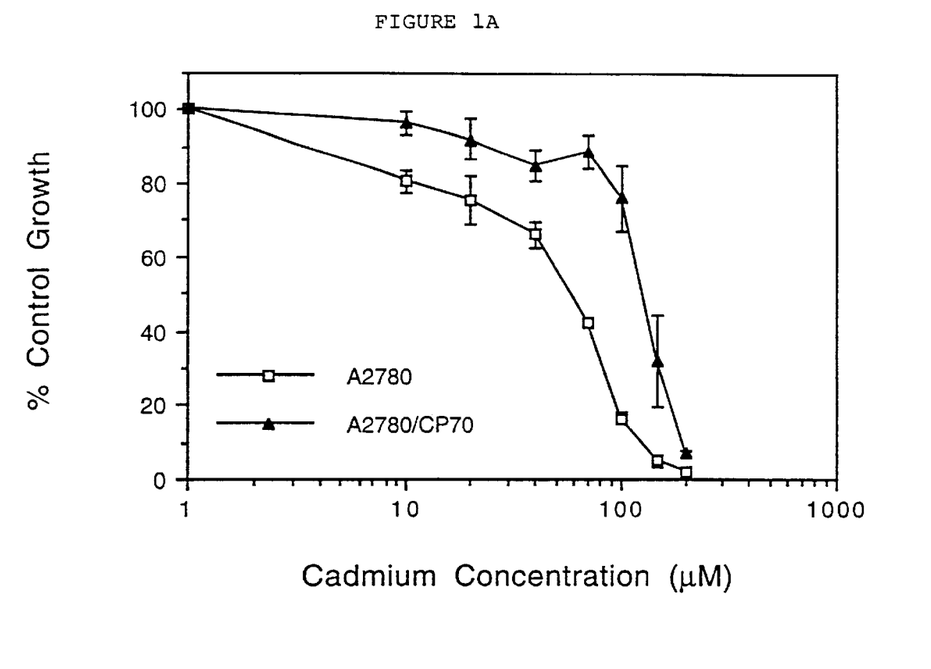
FIGS. 1A and 1B—Dose response curves of A2780 cell and A2780/CP70 cell lines following one hour treatments with various concentrations of $CdCl_2$ (FIG. 1A) or cisplatin (FIG. 1B). Cisplatin experiments are shown for comparison purposes. The drug concentrations that are effective for $CdCl_2$ are in the same range as for cisplatin. Adherent monolayers of A2780 (open squares) and A2780/CP70 (closed triangles) cells were assessed for sensitivity to Cd by the microculture tetrazolium assay, as described in "Materials and Methods". Each data point is the mean and standard deviation of four separate experiments.
Figure 1B:
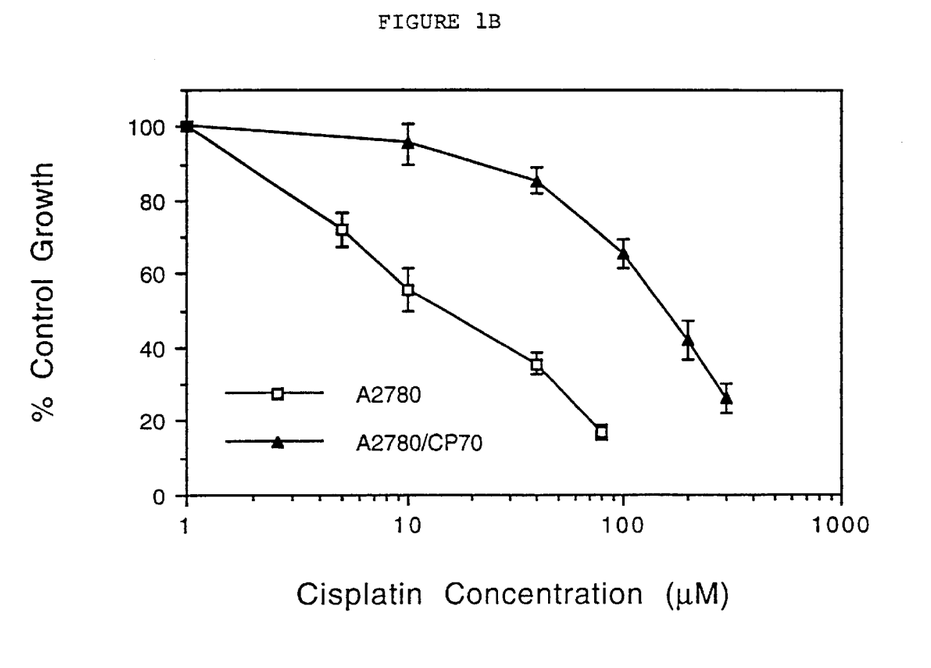

The relative sensitivities of the A2780 and A2780/CP70 cell lines to Cd and to cisplatin are shown in FIG. 1, and each data point is the mean and standard deviation of four or six separate determinations. After 1 hour exposures to various Cd drug doses, in the A2780 cell line (FIG. 1A; open squares), 10% cell kill occurred at 0.45 μM; 50% cell kill at 58 μM; and 90% cell kill at 130 μM. In the A2780/CP70 cell line (FIG. 1A; closed triangles), 10% cell kill was observed at 28 μM; 50% cell kill at 128 μM; and 90% cell kill at 195 μM.

The relative sensitivities of these cells to cisplatin were assessed in the same assay. As shown in FIG. 1B, the $IC_{50}$ for A2780 was 16 μM and for A2780/CP70 cells, 160 μM. In comparing the drug exposures associated with 50% cell kill, cisplatin resistant A2780/CP70 cells express a 10-fold increase in resistance to cisplatin as compared to A2780 cells, and an approximately equal level of "cross-resistance" to Cd. The A2780 cells are 3.6-fold more sensitive to cisplatin than to Cd on a μM basis, and A2780/CP70 cells are only slightly (1.25-fold) more sensitive to Cd.

2.2 Assessment of Total Cellular Accumulation of Cadmium

Figure 2:
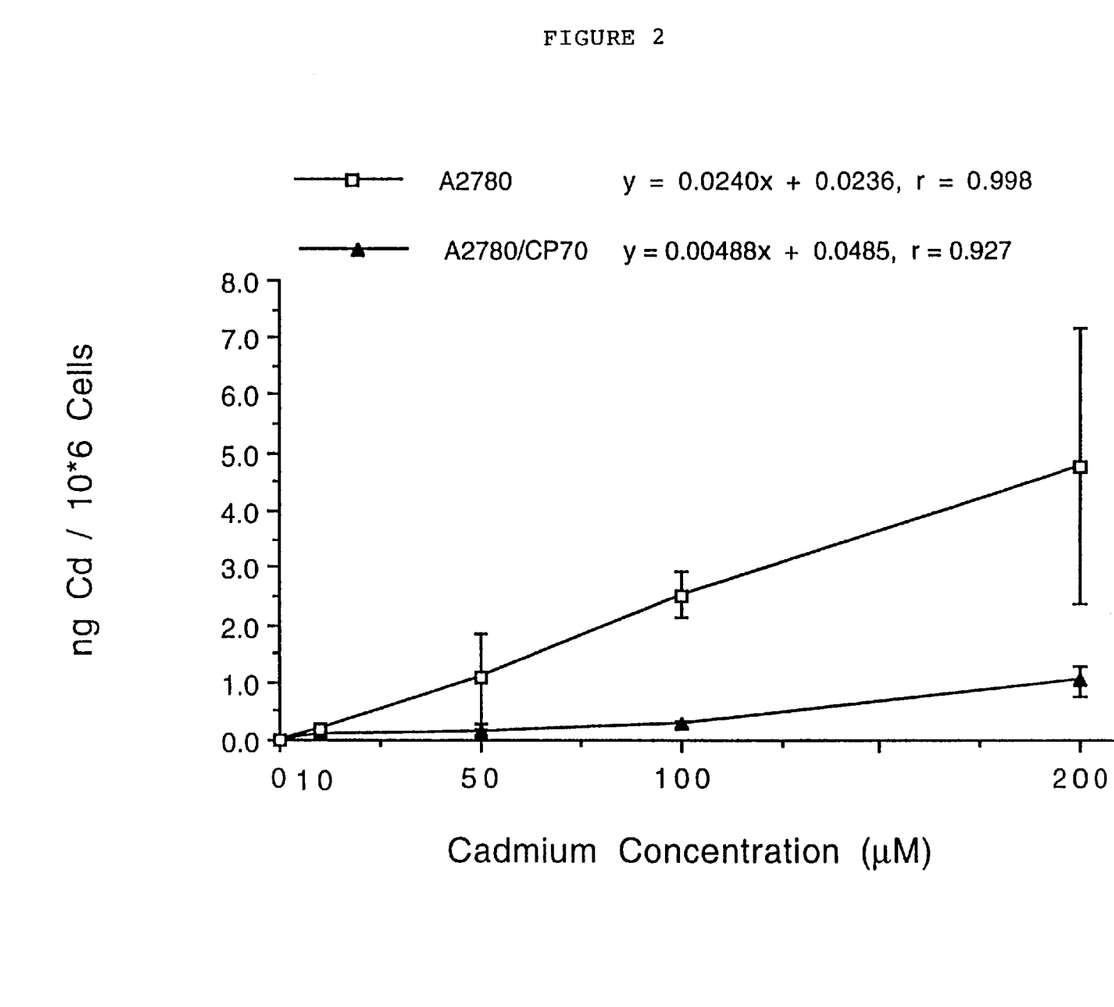
FIG. 2—Cellular drug accumulation of Cd in A2780 cells (open squares) and A2780/CP70 cells (closed triangles) following treatment with a range of CdCl drug doses. Each data point is the mean and standard deviation of six separate determinations.

We measured cellular accumulation of Cd in the two cell lines after exposure to defined drug doses, and these data are shown in FIG. 2. Each data point represents the mean±SD of three to six separate determinations. In both cell lines, there is an increase in cellular Cd with increasing concentration which approaches linearity. In A2780/CP70 cells, linear regression analysis up to the dose of 200 μM yields the equation y=0.005x+0.049 (r=0.93). In A2780 cells, there was a much greater increase in cellular drug levels over the range of Cd doses, and the linear regression equation is y=0.024x+0.024 (r=0.99). The slopes of the linear regression equations indicate that A2780 cells accumulate 4.9-fold more cellular drug per unit dose, as compared to A2780/CP70 cells.

2.3 Measurement of Rates of Cellular Drug Accumulation and Efflux

Figure 3A:
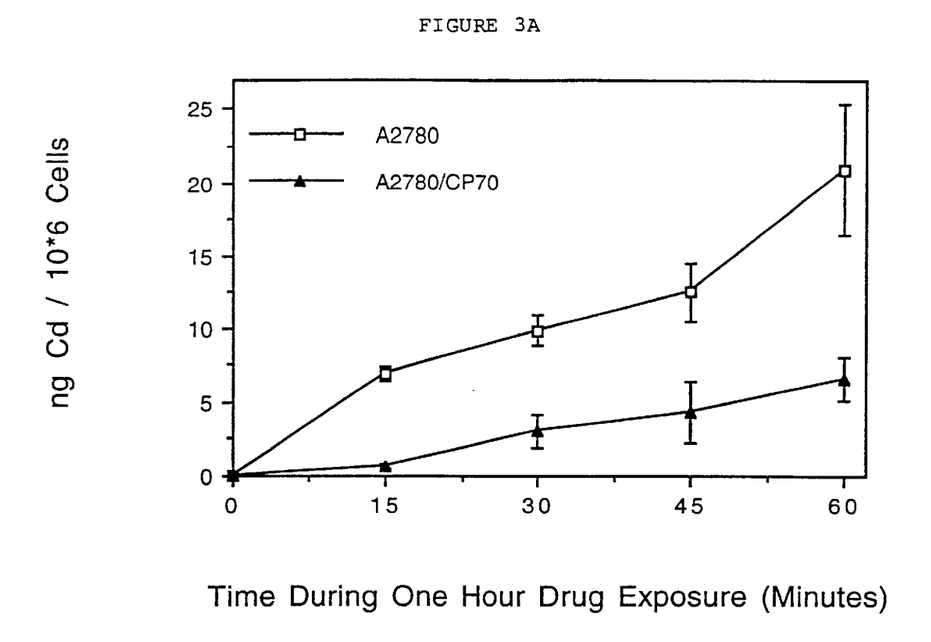
FIGS. 3A and 3B—Cellular accumulation and efflux of Cd in A2780 (open squares) and A2780/CP70 cells (closed triangles). Cells were exposed to their respective $IC_{50}$ doses and, at designated time points during the 1 hour exposure period, the total amount of cellular drug was measured.

To assess Cd drug uptake and efflux profiles of A2780 and A2780/CP70 cells, we measured the rate of total Cd drug accumulation during and after 1 hour exposures to their respective $IC_{50}$ drug doses. Accumulation values given are the mean and standard deviation of four separate experiments. As shown in FIG. 3A (Table 1), the relationship between cellular accumulation and time approaches linearity in both cell lines. For A2780 cells, linear regression analysis of these data yields the equation y=0.315x+0.552 (r=0.98). For A2780/CP70 cells, the equation is y=0.113x+0.458 (r=0.99). Based on the slopes of the curves, A2780 cells accumulate Cd drug at a 2.8-fold greater rate as compared to A2780/CP70 cells.

Figure 3B:
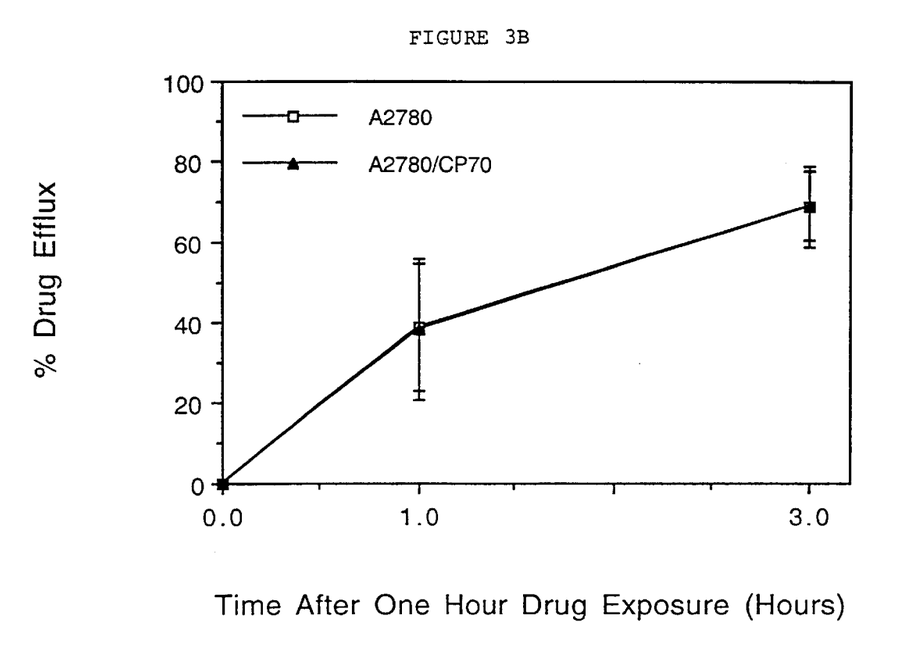

After 1 hour exposures to their respective $IC_{50}$ doses, the total cellular drug in A2780 cells was 20.85±4.49 ng Cd/$10^6$ cells, and in A2780/CP70 cells 6.61±1.48 ng Cd/$10^6$ cells. Over the observation period of 3 hours after a 1 hour exposure to $IC_{50}$(drug doses, A2780 cells retained 6.56±0.58 ng Cd/$10^6$ cells of total cellular drug (69% efflux) and A2780/CP70 cells retained 2.08±0.92 ng Cd/$10^6$ cells (69% efflux). When the rates of total drug accumulation and efflux were assessed as percentage of maximal drug, the rates of drug accumulation (FIG. 3A) and drug efflux (FIG. 3B and Table 2) were similar in the two cell lines.

2.4 Cadmium-DNA Adduct Formation

Figure 4:
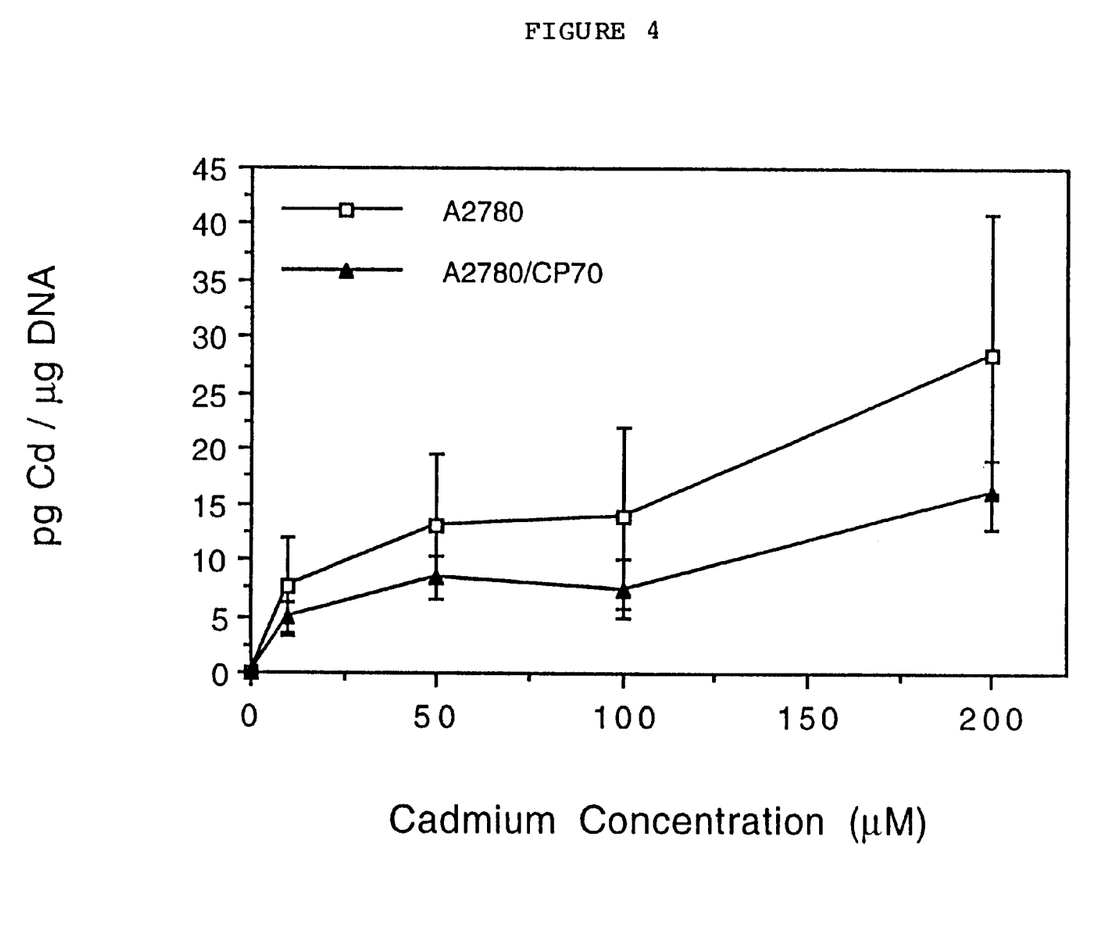
FIG. 4—Cd-DNA adduct formation profiles of A2780 cells line (open squares) and A2780/CP70 cell line (closed triangles) following equimolar treatments with a range of CdCl drug doses.

The level of Cd-DNA binding after equimolar Cd drug exposures are shown in FIG. 4 (Table 3), and represent the mean and standard deviation of three or four separate determinations. In cisplatin sensitive A2780 cells (open squares), Cd-DNA adduct formation increases with increasing Cd concentration, such that the relation between drug dose and adduct level approaches linearity (y=0.120x+3.850, r=0.92). For the cisplatin resistant A2780/CP70 cells (closed triangles), the relation between adduct level and Cd drug concentration also approaches linearity (y=0.070x+2.560, r=0.86). Based on the slopes of the equations, 1.7-fold more cellular Cd is needed in the A2780/CP70 cell line to attain the same level of Cd-DNA damage as in the A2780 cell line.

2.5 Cadmium DNA-Adduct and Repair

After treatment for 1 hour at their relative $IC_{50}$ doses of 58 μM for A2780 cells and 128 μM for A2780/CP70 cells, the two cell lines were compared for their respective ability to remove Cd-DNA adducts from cellular DNA over a 24 hour time period (Table 4). In A2780/CP70 cells, after a 1 hour $IC_{50}$ exposure, the peak adduct level measured was 15.58±3.56 pg Cd/μg DNA. At 6 hours after exposure, adduct was reduced to a level of 12.05±3.98 pg Cd/μg DNA, and at the end of the 24-hour observation period, 8.47±2.85 pg Cd/μg DNA of adduct remained. In A2780 cells, there was no removal of Cd from cellular DNA at 1 hour after its $IC_{50}$ exposure, at which time the peak adduct level was measured at 11.81±6.59 pg Cd/μg DNA. At 6 hours after Cd exposure, adduct levels were measured at 7.08±3.92 pg Cd/μg DNA. Adduct removal continued during the remainder of the 24-hour observation period, at which time levels were measured at 5.28±3.11 pg Cd/µg DNA.

When assessed as a percentage of the maximal value of Cd bound to DNA, the cisplatin resistant A2780/CP70 cell line removed 23% of the maximal adduct load after the first 6 hours, and the parental cisplatin sensitive A2780 cell line removed 40% of the maximal adduct. At the end of the 24-hour observation period, A2780/CP70 cells had removed 46% of Cd from cellular DNA, and A2780 cells had removed 55%. Data are utilized from FIG. 1A (Cd growth curves), FIG. 2 (cellular uptake curve), and table 3 (DNA adduct formation), to generate FIG. 5, panels A and B. In 5A, intracellular Cd concentrations are plotted against Cd-DNA damage levels for the two cell lines. As shown, there is no substantial difference between these two cell lines with respect to the relationship between intracellular drug and total DNA damage levels, up through an intracellular drug level of 1 ng per million cells.

In 5B, Cd-DNA damage levels are plotted against percent cell kill in the respective cell lines. This plot shows two features. There is a direct relationship between Cd-DNA damage levels and cell kill in both cell lines. Secondly, the curve for A2780/CP70 cells is shifted to the right of the A2780 curve; suggesting that in the resistant cells, more DNA damage is required to induce an equivalent level of cell kill (about 5–10 lesions more, per million DNA bases).

Collectively, these data suggest that the A2780/CP70 cell line's relative level of increased resistance to Cd, is based on two factors. One factor is decreased uptake of drug for the same level of drug exposure. Another factor is increased tolerance for equivalent levels of DNA damage. Cytosolic inactivation of drug appears not to be a major factor (see FIG. 5A); and DNA repair of total genomic DNA appears not to be a major factor (see table 4). Differences in gene-specific repair have not been ruled out.

TABLE 1

Cellular Accumulation of Cadmium in Human Ovarian Cancer A2780 and A2780/CP70 Cell Lines

| TIME MINUTES | CELL LINES | DRUG UPTAKE ng Cd/$10^6$ | PERCENT ACCUMULATION |
|---|---|---|---|
| 15 | A2780 | 6.89 ± 0.53 | 33 |
| 30 | A2780 | 9.83 ± 1.06 | 47 |
| 45 | A2780 | 12.47 ± 1.95 | 60 |
| 60 | A2780 | 20.85 ± 4.49 | 100 |
| 15 | A2780/CP70 | 0.65 ± 0.16 | 10 |
| 30 | A2780/CP70 | 3.03 ± 1.11 | 46 |
| 45 | A2780/CP70 | 4.33 ± 2.02 | 66 |
| 60 | A2780/CP70 | 6.61 ± 1.48 | 100 |

TABLE 2

Cellular Efflux of Cadmium in Human Ovarian Cancer A2780 and A2780/CP70 Cell Lines

| TIME HOURS | CELL LINES | ASSOCIATED DRUG ng Cd/$10^6$ Cells | PERCENT REMOVED |
|---|---|---|---|
| 0 | A2780 | 20.85 ± 4.4 | 90 |
| 1 | A2780 | 12.74 ± 3.74 | 30 |
| 3 | A2780 | 6.56 ± 0.58 | 69 |
| 0 | A2780/CP70 | 6.61 ± 1.4 | 80 |
| 1 | A2780/CP70 | 4.08 ± 1.4 | 38 |
| 3 | A2780/CP70 | 2.08 ± 0.92 | 69 |

TABLE 3

Cadmium-DNA Adduct Formation in Human Ovarian Cancer A2780 and A2780/CP70 Cell Lines After One Hour Exposure to Various Concentrations of Cadmium

| Cd µM | CELL LINES | pg Cd/ug DNA | fmol Cd/ug DNA | LESIONS/$10^6$ NEUCLEO-TIDES |
|---|---|---|---|---|
| 0 | A2780 | 0 | 0 | 0 |
| 10 | A2780 | 7.84 ± 4.26 | 42.77 ± 23.24 | 13.47 |
| 50 | A2780 | 13.01 ± 6.44 | 70.97 ± 35.13 | 22.35 |
| 100 | A2780 | 13.84 ± 8.12 | 75.50 ± 44.29 | 23.78 |
| 200 | A2780 | 28.36 ± 12.48 | 154.7 ± 60.08 | 48.72 |
| 0 | A2780/CP70 | 0 | 0 | 0 |
| 10 | A2780/CP70 | 4.81 ± 1.3 | 26.24 ± 7.09 | 8.26 |
| 50 | A2780/CP70 | 8.43 ± 1.9 | 45.99 ± 10.36 | 14.48 |
| 100 | A2780/CP70 | 7.42 ± 2.48 | 40.48 ± 13.53 | 12.75 |
| 200 | A2780/CP70 | 15.93 ± 3.08 | 86.90 ± 16.08 | 27.37 |

TABLE 4

Cadmium-DNA Adduct Repair in Human Ovarian Cancer A2780 and A2780/CP70 Cell Lines After One Hour Drug Exposure

| TIME HOURS | CELL LINES | Cd-DNA ADDUCT | fmol Cd/ug DNA | LESIONS $10^6$ NEUCLEOTIDES | % REPAIR* |
|---|---|---|---|---|---|
| 0 | A2780 | 8.45 ± 3.59 | 46.11 ± 19.60 | 14.52 | 0 |
| 1 | A2780 | 11.81 ± 6.59 | 64.39 ± 35.99 | 20.28 | 0 |
| 6 | A2780 | 7.08 ± 3.92 | 38.60 ± 21.37 | 12.16 | 40 |
| 24 | A2780 | 5.28 ± 3.11 | 20.80 ± 16.97 | 9.07 | 55 |
| 0 | A2780/CP70 | 15.58 ± 3.56 | 84.97 ± 19.41 | 26.76 | 0 |
| 1 | A2780/CP70 | 13.31 ± 4.62 | 72.58 ± 25.22 | 22.86 | 15 |
| 6 | A2780/CP70 | 12.05 ± 3.98 | 65.66 ± 21.78 | 20.68 | 23 |
| 24 | A2780/CP70 | 8.47 ± 2.85 | 46.22 ± 15.55 | 14.56 | 46 |

*Percentage repair reflects amount of peak adduct removed at designated time points.

III. Pharmaceutical Compositions

Generally the method of treating ovarian cancer with cadmium encompassed by the present invention, comprises administering to a human or another mammalian patient suffering from ovarian cancer, an effective ovarian cancer treating amount of a pharmaceutically acceptable cadmium containing compound. Exemplary of such cadmium containing compounds are various organic and inorganic salts of cadmium, including cadmium acetate, cadmium carbonate, cadmium bromide, cadmium chloride, cadmium fluoride, cadmium iodide, cadmium nitrate, cadmium oxide, cadmium hydroxide, cadmium salicylate, cadmium selenate, cadmium selenide, cadmium salicylate, cadmium succinate, cadmium sulfate, cadmium sulfide, and the like. Preferably the cadmium containing compound is cadmium chloride ($CdCl_2$).

In order to practice the advantageous method of the present invention, the cadmium containing compound is administered internally to the patient to be treated preferably in the form of a pharmaceutical composition which comprises the pharmaceutically acceptable cadmium containing compound in combination with a pharmaceutically acceptable carrier, which is chosen appropriately enough according to the route of administration which is desired for the cadmium containing compound, as well as other various factors such as compositional stability, and the like.

The cadmium containing compound is administered orally, subcutaneously, intravenously, intramuscularly, or parenterally, and usually in repeated doses until a satisfactory response is obtained. The daily dosage of the cadmium containing compound used to treat ovarian cancer in a patient suffering from ovarian cancer, will of course vary according to the exact etiology of the ovarian cancer being treated as well as the stage of the cancer in the patient, and the physical condition of the patient. However, generally it is envisioned that a pharmaceutical composition of the present invention will contain therein a sufficient amount of a pharmaceutically acceptable cadmium containing compound to provide about 1 to about 300 $mg/m^2$, preferably about 5 mg to about 200 $mg/m^2$, and most preferably about 10 to about 150 $mg/m^2$, of cadmium therein to the patient being treated, when the patient is a human adult female of about 1.5 to $2.2/m^2$ weighing about 50 kg, and wherein the composition is being administered by either an intravenous, oral, subcutaneously, intramuscular, or parenteral route of administration.

The pharmaceutical compositions of the present invention preferably contain from about 5 mg to about 100 mg of cadmium therein, and advantageously from about 5 mg to about 50 mg of cadmium therein per unit dose. In such a manner the cadmium containing compounds useful in the present inventive methods are presented in a therapeutic composition suitable for oral, parenteral, subcutaneous, intramuscular, intraperitoneal, or intravenous administration. Thus for example, compositions for oral administration can take the form of elixirs, capsules, tablets, or coated tablets containing carriers conventionally used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone. For parenteral administration the carrier or excipient can be comprised of a sterile parenterally acceptable liquid, such as water or arachis oil in ampoules.

Because the present inventive methods also envision optionally administering cisplatin, in combination with cadmium, to a patient suffering from ovarian cancer, it is also envisioned that in such instances the cisplatin should be administered to the patient in need thereof, in the form of a pharmaceutically acceptable composition containing a pharmaceutically acceptable carrier for the cisplatin. Methods of administering cisplatin to a patient for the treatment of cancers, and more specifically ovarian cancers, are known in the art, as are appropriate pharmaceutical compositions containing cisplatin for such uses. However, it is noted that when cisplatin is to be administered to a patient to treat ovarian cancer in combination with cadmium as herein described, then the total amount of cadmium and cisplatin being administered daily to the patient should usually not exceed the amounts indicated above for cadmium (i.e., about 300 $mg/m^2$ of cadmium). In this manner it is envisioned that possible side effects which might otherwise be associated with the administration of these active agents, either alone or in combination, are minimized, while at the same time allowing for an advantageous treatment regiment against the ovarian cancer in the patient. The specific amount of each active compound being administered to the patient will in any event be chosen in accordance with accepted medical and therapeutic procedures, as is usually done by a physician and veterinarian skilled in the field of cancer treatment, and more specifically the field of ovarian cancer treatment.

IV. Pharmaceutical Kits

The present invention also provides for pharmaceutical kits which allow one killed in the art to advantageously practice the cancer treatment methods encompassed by the present invention. The kits encompassed by the present invention generally comprise the following components:

(a) an effective ovarian cancer treating amount of cadmium in combination with a pharmaceutically acceptable carrier therefor;

(b) optionally, an effective ovarian cancer treating amount of cisplatin in combination with a pharmaceutically acceptable carrier therefor; and (c) instructions for carrying out a method of treating ovarian cancer in a human or other mammalian patient suffering from said ovarian cancer, the method comprising:

administering to said patient said pharmaceutical composition comprising said effective ovarian cancer treating amount of cadmium, and optionally, administering to said patient said pharmaceutical composition comprising said effective ovarian cancer treating amount of cisplatin.

When components (a) and (b) are both present in the kits, they are preferably present as spatially separate pharmaceutical compositions, and if appropriate even provided in spatially separate suitable containers. The instructions provided in the kit should be suitable to allow a physician, or if appropriate a veterinarian, to practice the present invention, utilizing the compositional components (a) and optionally (b) that are present in the kit. The instructions are preferably in a written or printed format, although other formats such as a computer disk for a computer would also be acceptable.

While the present disclosure is concerned primarily with treating ovarian cancer in a patient suffering therefrom, it is also envisioned that the methods, pharmaceutical compositions, and pharmaceutical kits disclosed herein can be advantageously used to treat cancers other than ovarian cancer in a human or other mammalian species suffering therefrom. For example, it is envisioned that one can administer a cadmium containing compound as provided for herein in an amount of about 1 to about 300 mg/m² to a human patient suffering from cancer, and thereby effectively treat said cancer.

V. References
(List of Publications and Other Documents Cited in the Present Disclosure)
1. Waalkes, M. P., C, T. P. and Barter, R. A. (1992) Toxicological principles of metal carcinogenesis with emphasis on cadmium. Critical Reviews in Toxicol, 22(3, 4), 175–201.
2. Gunn, S. A. and Gould, T. C. (1967). Specificity of response in relation to cadmium, zinc and selenium. In selenium in Biomedicine, eds. O. H. Muth, J. E. Oldfield and P. H. Weswig. pp.395–413.
3. Jungman, J., Reins, H. A., Schobert, C. and Jentsch, S. (1993). Resistance to cadmium mediated by ubiquitin-dependant proteolysis. Nature, 361, 369–371.
4. Waalkes, M. P., Diwan, B. A., C, T. P., Weghorst, C. M., Ward, J. M., Shiraishi, N., Rice, J. M., Cherian, M. G. and Goyer, R. A. (1993) The tumor suppressive activity of cadmium. Metallothionein, Birkhauser Verlag, Basel, Switzerland.
5. Wasserman, K., Piesel, M., Bohr, V. A. (1992) Overexpression of metallothionein in Chinese hamster ovary cells and its effect on nitrogen mustard-induced cytotoxicity: role of gene-specific damage and repair. Cancer Res, 52, 6853–6859.
6. Sciavolino, P. J., Lee, T. H. and Vilcek, J. (1992) Overexpression of metallothionein confers resistance to the cytotoxic effect of TNF with cadmium in MCF-7 breast carcinoma cells. Lymphokine and Cytokine Research, 11(5), 265–270.
7. Morton, K. A., Jones, B. J., Sohn, M. H. and Schaefer, A. E. (1992). Uptake of cadmium is diminished in transfected mouse NIH/3T3 cells enriched for metallothionein. J. Biol. Chem, 267, 2880–2883.
8. Moffatt, P., Marion, M. and Denizeau, F. (1992) Cadmium-2-acetylaminofluorene interaction in isolated rat hepatocytes. Cell. Biol. Toxicol, 8, No. 4, 277–290.
9. Wahba, Z. Z., C, T. P., Rhodes, S. W. and Waalkes, M. P. (1993). Protective effects of selenium on cadmium toxicity in rats: Role of altered toxicokinetics and metallothionein. J. Toxicol. Exp. Health, 38, 171–182.
10. Shiraishi, N., Barter, R. A., Uno, H. and Waalkes, M. P. (1993). Effect of progesterone pretreatment on cadmium toxicity in the male Fischer (F344/NCr) rat[1]. Toxicol. Appl. Pharmacol, 118, 113–118.
11. Hartwig, A., and Beyersman, D. (1989). Comutagenicity and inhibition of DNA repair by metal ions in mammalian cells. Biological Trace Element Research, 21, 359–365.
12. Nocentini, S. (1987) Inhibition of DNA replication and repair by cadmium in mammalian cells. Protective interaction of zinc. Nucleic Acids Res, 15, 4211–4225.
13. Collins, J. F., Brown, J. P., Painter, P. R., Jamall, I. S., Zeise, L. A., Alexeeff, G. V., Wade, M. J., Siegel, D. M and Wong, J. J. (1992) On the carcinogenicity of cadmium by the oral route. Regul. Toxicol. Pharmacol, 16, 57–72.
14. Ochi, T., Ishiguro, T. and Ohsawa, M. (1983) Participation of active oxygen species in the induction of DNA single-strand scissions by cadmium chloride in cultured Chinese hamster cells. Mutat. Res, 122, 169–175.
15. Poirier, L. A., Kasprzak, K. S., Hoover, H. and Wenk, M. L. (1983). Effects of calcium and magnesium acetates on the carcinogenicity of cadmium chloride in Wistar rats. Cancer. Res, 43, 4575–4581.
16. Waalkes, M. P., Diwan, B. A., Weghorst, C. M,., Bare, R. M., Ward, J. M. and J. M. Rice, J. M (1991) Anticarcinogenic effects of cadmium in B6C3F1 mouse liver and lung. Toxicol. Appl. Pharmacol, 110, 327–335.
17. Behrens, B. C., Hamilton, T. C., Masuda, H., Grotzinger, K. R., Whang-Peng, J., Louie, K. G., Knudsen, T., McKoy, W. M., Young, R. C. and Ozols, R. F. (1987) Characterization of a cis-Diaminedichloroplatinum(II)-resistant human ovarian cancer cell line and its use in evaluation of platinum analogues. Cancer. Res, 47, 414–418.
18. Parker, R. J., Eastman, A., Bostic-Bruton, F. and Reed, E. (1991). Acquired cisplatin resistance in human ovarian cancer cells is associated with enhanced repair of cisplatin-DNA lesions and reduced drug accumulation. J. Clin. Invest, 8, 772–7777.
19. Alley, M. C., Scudiero, M. A., Monkes, A., Hursey, M. L., Czerwinsk, M. J., Fine, D. L., Abbot, B. J., Mayo, J. G., Shoemaker, R. H. and Boyd, M. R. (1988) Feasibility of drug screening with panels of human tumor cell lines using a microculture tetrazolium assay. Cancer Res, 47, 589–601.
20. McGahan, M. C. and Tyczkowska, K. (1987) The determination of platinum in biological materials by electrothermal atomic absorption spectroscopy. Spectrochim. Acta, 42B, 665–668.
21. Parker, R. J., Lee, K. B. and Reed, E. (1994). Methods development for the measurement of cadmium chloride (Cd) in biological materials. Proc. Am. Asso. Cancer Res, 35, Abstract# 2456.
22. Flamm, W. G., Birnistiel, M. L. and Walter, P. M. B. (1969) Subcellular Components. Preparation and fractionation. G. Birnie and S. M. Fox, editors. Butterworth and Co., Ltd., London pp. 129–155.
23. Waalkes, M. P. and Rehm, S. (1992). Carcinogenicity of oral cadmium in the male Wistar (WF/Ncr) rat: Effect of chronic dietary zinc deficiency. Fundamen. Appl. Toxicol, 19, 512–520.
24. Webb, M. (1979) Ed. in the Chemistry, Biochemistry and Biology of Cadmium. Elsevier/North-Holland, Amsterdam.
25. Verma, M. P., Scharma, R. O. and Bourcier, D. R. (1982). Macromolecular interactions with cadmium and the effect of zinc, copper, lead and mercury ions. Biol. trace Element. Res, 4, 35–43.
26. Waalkes, M. P. and Poirier, L. A. (1984) In vitro cadmium-DNA interactions: Cooperativity of cadmium binding and competitive antagonism by calcium, magnesium, and zinc. Poirier. Toxicol. Appl. Pharmacol, 75, 539–546.
27. Sunderman, F. W., Jr. and Barber, A. M. (1988). Finger-loop, oncogen, and metals. Ann. Clin. Lab. Sci, 18, 267–288.
28. Ochi, T., Mogi, M., Watanabe, M. and Ohsawa, M. (1984). Induction of chromosomal aberrations in cultured Chinese hamster cells by short-term treatment with cadmium chloride. Mutat. Res, 137, 103–109.
29. Ochi, T., Takahashi, K. and Ohsawa, M. (1987). Indirect evidence for the induction of a prooxidant state by cadmium chloride in cultured mammalian cells and a possible mechanism for the induction. Mutat. Res, 180, 257–266.
30. Snyder, R. D. (1988). Role of active oxygen species in metal-induced DNA strand breakage in human diploid fibroblasts. Mutat. Res, 193, 237–246.
32. Johnson, A. D., Sigman, M. B. and Miller, W. J. (1970) Early action of cadmium in the rat and domestic fowl testes. III. Subcellular location of injected cadmium. J. Reprod. Fertil, 23, 201–213.
33. Bryan, S. E. and Hidalgo, H. A. (1967). Nuclear cadmium: Uptake and disappearance correlated with cadmium-binding protein synthesis. Biochem. Biophys. Res. Commun, 68, 858–866.
33. Eichhorn, G. L. and Shin, Y. A. (1968). Interactions of metal ions with polynucleotides and related compounds, XII. The relative effect of various metal ions on DNA helicity. J. Amer. Chem. Soc, 90, 7323–7328.
34. Williams, D. R. (1972) Metals, ligands, and cancer. Chem. Rev, 72, 203–213.
35. Furst, T. (1981) Bioassay of metals for carcinogenesis: Whole animals. Environ. Health Perspect, 40, 83–91.
36. Gunn, S. A., Gould, T. C. and Anderson, W. A. D. (1963). Cadmium-induced interstitial cell tumors in rat and mice and their prevention by zinc. J. Natl. Cancer Inst, 31, 745–759.

Each of the publications listed above is incorporated herein by reference in its entirety.

What is claimed is:

1. A method of treating ovarian cancer in a human or other mammalian patient suffering from said ovarian cancer, the method consisting essentially of:
   administering to said patient an effective ovarian cancer treating amount of a cadmium containing compound, and administering to said patient an effective ovarian cancer treating amount of cisplatin.

2. The method of treating ovarian cancer as recited in claim 1, wherein said patient is a human.

3. A method of treating ovarian cancer in a human or other mammalian patient suffering from said ovarian cancer, the method consisting essentially of:
   administering to said patient an effective ovarian cancer treating amount of a cadmium containing compound.

4. The method of treating ovarian cancer as recited in claim 3, wherein said patient is a human.

5. The method of treating ovarian cancer as recited in claims 3, wherein said cadmium containing compound is selected from the group consisting of cadmium acetate, cadmium carbonate, cadmium bromide, cadmium chloride, cadmium fluoride, cadmium iodide, cadmium nitrate, cadmium oxide, cadmium hydroxide, cadmium salicylate, cadmium selenate, cadmium selenide, cadmium salicylate, cadmium succinate, cadmium sulfate and cadmium sulfide.

6. The method of treating ovarian cancer as recited in claim 3, wherein said cadmium containing compound is cadmium chloride.

7. A pharmaceutical composition consisting essentially of:
   (a) an enhanced effective ovarian cancer treating amount of cadmium chloride; and
   (b) an enhanced effective ovarian cancer treating amount of cisplatin in combination with a pharmaceutically acceptable carrier for intravenous administration.

* * * * *